United States Patent [19]

Vukics et al.

[11] Patent Number: 6,034,274
[45] Date of Patent: Mar. 7, 2000

[54] PROCESS FOR PREPARING A NAPHTALENAMINE DERIVATIVE

[75] Inventors: Krisztina Vukics; Tamas Fodor; Janos Fischer; Iren Fellegvari, all of Budapest; Sandor Levai, Biatorbagy, all of Hungary

[73] Assignee: Richter Gedeon, Hungary

[21] Appl. No.: 09/319,879

[22] PCT Filed: Dec. 15, 1997

[86] PCT No.: PCT/HU97/00083

§ 371 Date: Jul. 27, 1999

§ 102(e) Date: Jul. 27, 1999

[87] PCT Pub. No.: WO98/27050

PCT Pub. Date: Jun. 25, 1998

[30] Foreign Application Priority Data

Dec. 18, 1996 [HU] Hungary ................................. 9603493

[51] Int. Cl.[7] ................................................. C06C 211/00
[52] U.S. Cl. ........................................... 564/308; 564/300
[58] Field of Search ..................................... 564/300, 308

[56] References Cited

U.S. PATENT DOCUMENTS 5,248,699  9/1993  Sysko et al. .

FOREIGN PATENT DOCUMENTS 2105393  9/1992  Canada .
0028901  5/1981  European Pat. Off. .
030 081   6/1981  European Pat. Off. .

OTHER PUBLICATIONS

Tremaine, L et al, Drug Metab, Dispos. (1989) 17(5) 542–50.

*Primary Examiner*—Paul J. Killos
*Attorney, Agent, or Firm*—Keil & Weinkauf

[57] ABSTRACT

The present invention relates to a process for preparing cis-(1S)-N-methyl-4-(3,4-dichlorophenyl)-1,2,3,4-tetrahydro-1-naphtalenamine and its acid addition salts wherein N-methyl-[4-(3,4-dichlorophenyl)-1,2,3,4-tetrahydro-naphtalene-1-en]-amine-N-oxide is hydrogenated in an inert solvent in the presence of a catalyst, then the resulting mixture is treated with alcanolic solution of a mineral acid, the resulting cis-racemic acid addition salt is converted to the free base by known methods, resolved and the resulting cis-(+)-base of formula (II) is converted to an acid addition salt. N-methyl-[4-(3,4-dichlorophenyl)-1,2,3,4-tetrahydro-naphtalene-1-en]amine-N-oxide is also disclosed.

4 Claims, No Drawings

PROCESS FOR PREPARING A NAPHTALENAMINE DERIVATIVE

The present invention relates to a novel process for preparing a naphtalenamine derivative, the compound of formula (I) (chemical name: cis-(1S)-N-methyl-4-(3,4-dichloroplenyl-1,2,3,4-tetrahydro-1-naphtalenamine) hereinafter referred as to "sertraline" and its acid addition salts.

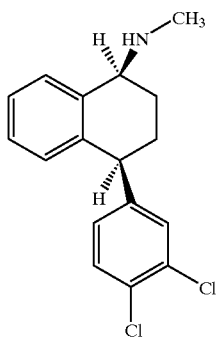

A novel intermedier used in this process, the compound of formula (II) is also disclosed.

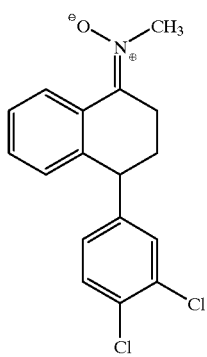

It is known that sertraline hydrochloride is a valuable pharmaceutically active substance, and the pharmaceutical composition containing this compound is applicable in the treatment of depression and other dependence and anxiety-related disorders (See U.S. Pat. Nos. 4,536,518 and 5,248,699).

The preparation of sertraline is reported in the above mentioned U.S. Pat. No. 4,536,518 (or the equivalent Hungarian patent No. 182,224). The essence of the herein described process is, that 4-(3,4-diclorophenyl)-3,4-dihydro-1-(2H)-naplitalene-1-on, which can be prepared in a complicated reaction way of several steps is condensed with methylamine to the Schiff base in the presence of titane tetrachloride as catalyst. The Schiff base is hydrogenated in the presence of palladitun on carbon as catalyst, and a mixture of the cis/trans isomers of N-methyl-4-(3,4-dichlorophenyl)-1,2,3,4-tetrahydro-1-naphtalenamine hydrochloride is obtained, where the cis/trans ratio is about 70:30. The mixture of cis/trans isomers is dissolved in a 40 times amount of hot methanol based on the starting tetralone, and the cis isomer in crystalline form can be obtained after the addition of a 30 times amount of diethyl ether. The primary yield is 48%, which is increased to 68% by working up the mother liquor obtaining a second crop of the title compound.

The disadvantages of the described process obviously appear from the above survey, namely, the appropriate diliydro-naphtalenone derivative can be prepared only in several steps with difficulties. Moreover, the hydrogenation of the Schiff-base derivative of this compound results in a mixture of cis/trans isomers. The desired cis-isomer from this mixture can be obtained only in large dilution and using big excess of solvents. The large-scale realization of this process is very disadvantageous, even without mentioning the working time, working power and energy excess made by the big solvent circulation and the work-up of the so-called secondary generation's mother liquor.

So the aim of the present invention is to produce a process which doesn't show the above disadvantages but at the same time gives sertraline or its acid addition salts in a simplier way and in better yield.

During our experiments, we found that reacting the appropriatly substituted 3,4-dihydro-naphtalenone derivative, that could be prepared in a simple way, with the commercially available N-methylhydroxylamine a so far in the literature not reported N-oxide derivative formed, which after isolation could give directly the desired cis-compound in catalytic hydrogenation, which was easily resolved and converted to sertraline.

This recognition is surprising because N-oxide derivatives similar to that compound of Formula (II) are unstable, and it was unexpected that exactly the desired stereoisoiner could be obtained by the hydrogenation.

According to the above, the invention relates to a process for preparing cis-(1S)-N--methyl-4-(3,4-dichlorophenyl)-1,2,3,4-tetrahydro-1-naphtalenamine of formula (I) and its acid addition salts, in the way, that N-methyl-[4-(3,4-dichlorophenyl)-1,2,3,4-tetrahydro-naphtalene-1-en]-amine-N-oxide of formula (II) is hydrogenated in an inert solvent in the presence of a catalyst, then the resulting mixture is treated with alcanolic solution of a mineral acid, the resulting cis-racemic acid addition salt is converted to the free cis-base by standard techniques well-known to those skilled in the art, resolved, then in the required case the cis-(+)-base of formula (I) is converted to the acid addition salt.

According to a preferred version of the process disclosed in the invention, methanol is used as inert solvent, and Raney-Nickel is used as catalyst in the hydrogenation.

According to the process disclosed in the invention, hydrogen chloride in methanol or ethanol is used as alcanolic solution of mineral acid.

Resolution of the racemic compound can be carried out with an optically active acid by standard tecniques well-known to those skilled in the art.

The invention also relates to the N-methyl-[4-(3,4-dichlorophenyl)-1,2,3,4-tetrahydro-naphtalene-1-en]-amine-N-oxide, which is a new, so far not reported compound.

The N-oxide of formula II can be prepared from 4-(3,4-dichlorophenyl)-3,4-dihydro-1-naphtalenone and commercially available N-methylhydroxylamine heating under reflux in an inert solvent, preferably in ethanol in 70–90% yield.

The starting material [4-(3,4-dichlorophenyl)-3,4-dihydro-1-naphtalenone] can be prepared by the reaction of 1-naphtol and 1,2-dichlorobenzene that gives the starting compound in the presence of aluminum chloride as catalyst in 80% yield. The above reaction of naphtol is previously reported by Rupinskaya and her co-workers in their article (Zh.Org.Khim. 18(4) 870–8 (1982).

The main advantage of the process of our invention is that the new N-oxide of formula (II) gives the compound of formula (I) in a far better yield compared with the former Schiff-base method. The bigger stability of the N-oxide compared to the Schiff base makes the isolation possible, which can be applied as purification step if required.

Finally, it is important in safety respects that instead of the harmful methylamine the harmless N-methylhydroxylamine is going to be applied.

The process disclosed in our invention is presented by the following examples:

EXAMPLE 1

Cis-N-methyl-4-(3,4-dichlorophenyl)-1,2,3,4-tetrahydro-1-naphtalenamine hydrochloride 11.2 g (35 mmol) of N-methyl-[4-(3,4-dichlorophenyl)-1,2,3,4-tetrahydro-naphtalene-1-en]-amine-N-oxide was suspended in 200 ml of methanol and hydrogenated over 3–4 g of Raney-Nickel catalyst washed to pH neutral and anhydrous at atmospheric pressure and 25° C. After the theoretically necessary hydrogen uptake had ceased (5–6 h), the catalyst was filtered, and the methanol was evaporated. The residue was dissolved in 60 ml of ethanol and 5.1 ml of 6.8 n hydrogen chloride in ethanol was added dropwise to the stired solution.

The title compound starts immediately crystallising. The suspension was stirred for 3 hours at 0° C., then filtered and washed with 30 ml of −10° C. ethanol.

Product: 11.5 g (81%) of the title compound. TLC: Kiselgel-60, ethyl acetate/methanol/cc. ammonium hydroxide 10:0.5:0.25, Rf: 0.54. Mp: 290–291° C.

EXAMPLE 2

In like manner to that described in Example 1, the same compound was prepared by hydrogenation using 20 times amount of ethanol based on N-oxide of formula (II) as solvent in the presence of 10% palladium on carbon as catalyst. The product obtained was identical in every respect with the product of Example 1.

PREPARATION OF THE STARTING MATERIALS a.) Preparation of 4-(3,4-dichlorophenyl)-3,4-dihydro-1 (2H)-naphtalene-1-on To a stirred solution of 21.62 g (0.15 mol) of 1-naphtol in 182 g (140 ml) of 1,2-dichloro-benzene 50 g (0.375 mol) anhydrous aluminum chloride was added. The reaction mixture was heated to 100° C. and stirred at this temperature for 1 hour. The mixture was cooled to room temperature and poured into 240 g of ice and 70 ml of cc. hydrochloric acid, then 200 ml of methylene chloride was added. The organic layer was separated and the aqueous layer was extracted twice with 200 ml of methylene chloride. The combined organic layers were washed with 200 ml of water and stirred with 20 g of celite and 10 g of activated carbon, filtered and the solvents were evaporated in vacuum. To the oily residue (45–50 g) 44 ml of methanol was added. The product crystallized, the suspension was stirred for 5 hours at 0° C., then filtered and washed twice with 50 ml of −10° C. methanol.

Product: 34.9 g (80%) of the title compound. TLC: Kiselgel-60, n-hexane/ethanol 10:1, Rf: 0.29. Mp: 99–101° C.

b.) Preparation of N-methyl-[4-(3,4-dichlorophenyl)-1,2,3, 4-tetrahydro-naphtalene-1-en]-amine-N-oxide [compound of formula (II)]

46.08 g (0.158 mol) of 4-(3,4-dichloro-phenyl)-3,4-dihidro-naphtalene-1-on, 26.45 g (0.317 mol) of N-methylhydroxylamine hydrochloride and 25.98 g (0.317 mol) of anhydrous sodium acetate in 600 ml of ethanol were stirred and heated until boiling. After 6 hour heating under reflux the ethanol was evaporated in vacuum in a 50° C. water bath. To the residue 200 ml of water and 200 ml of methylene chloride were added. The organic layer was washed with 100 ml of water, then the combined aqueous layers were extracted with 100 ml of methylene chloride.

The organic layer was dried on anhydrous sodium sulfate, filtered and the solvent was evaporated in vacuum in a 30° C. water bath. To the residue 65 ml of t-butyl methyl ether was added and stirred for 2 hours at room temperature and then for 4 hours at 0° C. The product was filtered and washed twice with 30 ml of −10° C. t-butyl methyl ether.

Product: 43.0 g (85%) of the title compound. TLC: Kieselgel-60, methylene chloride/methanol 10:1, Rf: 0.52. Mp: 175–179° C.

Further physical and chemical properties of the product are listed below:

NMR data:

NMR spectrum was recorded on a Varian VXR-300 spectrometer ($^1$H: 300 Hz) using $CDCl_3$ as solvent, temperature: 24° C., reference: δ=0.00 ppmn.

$^1$H-NMR: 2.10–2.30 m (2H) [1H-3], 2.50–2.80 m (2H) [H-2], 3.88 s (3H) [H-NMe], 4.12 t (1H) [H -4], 6.83 dd (1H) [H-16], 6.97 d (1H) [H-15], 7.19 d (1H) [H-12], 7.25–7.50 m (3H) [H-6,7,8], 9.63 d (1H) [H-9]

Mass Spectroscopic Data:

MS spectum was obtained using a VG-TRIO-2-spectrometer, ionization mode: EI, electron energy: 70 eV, ion source temperature: 250° C. m/z (rel. int. %): 323(6.0) [M+4]$^+$; 321(33.0) [M+2]$^+$; 319(49.0) [M]$^+$; 306(18.0); 304 (68.0); 302(100.0); 279(3.0); 277(13.0); 275(21.0); 206 (4.0); 204(23.0); 202(29.0); 160(20.0); 128(30.0); 115(33.0)

Infrared data:

Equipment: PERKIN ELMER 1000 spectrophotometer, phase: KBr pellet, resolution: 4 $cm^{-1}$.

The most characteristic absorption bands ($cm^{-1}$):

N→O 1470, 1201

C=N 1642 (weak)

Ar–Cl 1130, 1077

Ar 1588, 832, 767

Other important absorption bands ($cm^{-1}$):

2937, 1524, 1353, 1032, 949, 712, 560

Reference Example:

Preparation of cis-(1S)-N-methyl-4-(3,4-dichlorophenyl)-1,2,3,4-tetrahydro-1-naphtalanamine hydrochloride (sertraline hydrochloride)

10.27 g (30 mmol) of cis-N-methyl-4-(3,4-dichlorophenyl)-1,2,3,4-tetrahydro-1-naphtalenamine hydrochloride described in Example 1 was dissolved in 70 ml of methylene chloride and extracted with 40 ml of 10% aqueous sodium carbonate. The aqueous layer was extracted with 30 ml of methylene chloride, then the combined organic layers were dried on sodium sulfate and fitered. Methylene chloride was evaporated in vacuum in a 40° C. water bath. The residue was dissolved in 100 ml ethanol, and 4.56 g (30 mmol) R-(−)-mandelic acid was added. The mandelic acid salt crystallized after a few minutes. The resulting suspension was stirred for 6 hours at 25° C., then filtered and washed with 50 ml of ethanol.

Product: 5.65 g (41%) of cis-(1S)-N-methyl-4-(3,4-dichlorophenyl)-1,2,3,4-terahydro-1-naphtyl-amine mandelate, mp: 189–191° C.

5.04 g (11 mmol) of the above described mandelic acid salt was mixed with 50 ml of methylene chloride and 30 ml of 2 n aqueous sodium hydroxide. The layers were separated and the aqueous layer was extracted with 20 ml of methylene chloride. The combined organic layers were dried on sodium sulfate, filtered, and the solvent was evaporated in vacuum in a 40° C. water bath. The residue was dissolved in 30 ml of ethanol and during stiring 1.62 ml of 6.8 n hydrogen chloride in ethanol was added. The product immediately crystallized. The suspension was stirred for 5 hours at 0° C., then filtered, washed with 20 ml of −10° C. ethanol and dried.

Product: 3.2 g (85%) of the title compound (sertraline hydrochloride). Mp: 246–249° C.

We claim:

1. A process for preparing cis-(1S)-N-methyl-4-(3,4-dichlorophenyl)-1,2,3,4-tetrahydro-naphtalenamine and its acid addition salts, which comprises the steps of hydrogenating of N-methyl-[4-(3,4-dichlorophenyl)-1,2,3,4-tetrahydro-naphtalene-1-en]-amine-N-oxide of the formula (II) in an inert solvent in the presence of a catalyst, then treating the obtained mixture with alcanolic solution of hydrogen chloride, converting the resulting cis-racemic acid addition salt to the free base, resolving and converting the resulting cis-(+)-base of formula (I) to acid addition salt.

2. A process as claimed in claim 1 wherein the inert solvent is methanol, and the catalyst is Raney-Nickel catalyst in the hydrogenation.

3. A process as claimed in claim 1 wherein the alcoholic solution of inorganic acid is hydrogen chloride in methanol or ethanol.

4. N-methyl-[4-(3,4-dichlorophenyl)-1,2,3,4-tetrahydro-naphtalene-1-en]-amine-N-oxide.

* * * * *